(12) United States Patent
Rabinovich-Guilatt et al.

(10) Patent No.: US 8,227,452 B2
(45) Date of Patent: Jul. 24, 2012

(54) USE OF A STEROID PRODRUG FOR THE TREATMENT OF DISEASE OF THE POSTERIOR SEGMENT OF THE EYE

(75) Inventors: Laura Rabinovich-Guilatt, Kadima (IL); Gregory Lambert, Chatenay-Malabry (FR)

(73) Assignee: Novagali Pharma SA, Evry (FR)

( * ) Notice: Subject to any disclaimer, the term of this patent is extended or adjusted under 35 U.S.C. 154(b) by 641 days.

(21) Appl. No.: 11/806,554

(22) Filed: Jun. 1, 2007

(65) Prior Publication Data

US 2007/0280995 A1    Dec. 6, 2007

Related U.S. Application Data

(62) Division of application No. 11/444,337, filed on Jun. 1, 2006.

(30) Foreign Application Priority Data

Jun. 1, 2006    (EP) .................................... 06290902

(51) Int. Cl.
*A61K 31/56*    (2006.01)

(52) U.S. Cl. ........................................ 514/171; 514/182
(58) Field of Classification Search .................. 514/171, 514/182

See application file for complete search history.

(56) References Cited

U.S. PATENT DOCUMENTS

2006/0002963 A1 *  1/2006  Rabinovich-Guilatt et al. ............................ 424/400

FOREIGN PATENT DOCUMENTS

| EP | 0 244 178 | * 11/1987 |
| WO | WO90/01933 | * 3/1990 |
| WO | WO99/11270 | * 3/1999 |

OTHER PUBLICATIONS

Das et al., Br J Ophthalmol., 1999;83:1050-1055.*

* cited by examiner

*Primary Examiner* — San-Ming Hui
(74) *Attorney, Agent, or Firm* — Young & Thompson

(57) ABSTRACT

Use of a composition comprising at least one prodrug of a steroid, preferably of a corticosteroid, for the preparation of an ophthalmic composition intended for the treatment of an ocular condition or disease of a human being or an animal.

9 Claims, No Drawings

USE OF A STEROID PRODRUG FOR THE TREATMENT OF DISEASE OF THE POSTERIOR SEGMENT OF THE EYE

The present invention relates to the field of the treatment of the ophthalmic diseases, in particular of the intraocular diseases of a human being or an animal, by at least one steroid, and in particular by at least one corticosteroid.

The invention particularly focuses on ophthalmic compositions or devices, preferably ophthalmic emulsions, comprising at least one steroid, preferably a corticosteroid. The invention also relates to the administration of such ophthalmic compositions, and in particular to their administration intraocularly. The invention relates also to the controlled release of therapeutic active agents, in particular of corticosteroids intraocularly, in particular in the posterior segment of the eye.

A posterior ocular condition is a disease which primarily affects a posterior ocular site such as choroid or sclera, vitreous, vitreous chamber, retina, optic nerve, and blood vessels and nerves which vascularize or innervate a posterior ocular site.

Steroids are already largely used to treat ophthalmic diseases affecting the posterior chamber of the eye, in particular central retinal vein occlusion (CRVO), branch retinal vein occlusion (BRVO), choroidal macular edema (CME), diabetic macular edema (DME), diabetic macular retinopathy, uveitis, and age related macular degeneration (ARMD). These treatments generally imply their systemic administration, causing known side effects, which are significant, regarding the ophthalmic diseases to treat. These side effects singularly decrease the interest of the treatment of these ophthalmic diseases by systemic administration of steroids.

Other modes of administration, topic, suprachoroidal, subconjunctival, retrobulbar, and intravitreal were searched. Regarding topical application, dexamethasone penetration into the vitreous humour after repeated topical application is negligible (less than 2 ng/ml after 1 drop of 0.1% dexamethasone phosphate drops hourly for 10 hours) (Weijtens, Opthalmology, 2002). In comparison, serum and vitreous levels of 60 and 5 ng/ml respectively are observed following a single oral administration of 7.5 mg dexamethasone (Weijtens, Am J Opthalmol, 1998).

It was also shown that the subretinals concentrations of dexamethasone after subconjunctival or peribulbar injection were 120 and 13-fold more elevated than after oral administration (Weijtens et al. Opthalmology, 2000). The local intraocular administration is thus highly preferred.

However, the injection of steroids in significant amounts in the eye, implies a sudden and massive increase in their concentration in all ocular structures, and can also lead to undesirable and consequent local ocular side effects, in particular a significant increase in the intraocular pressure possibly leading to the development of glaucoma, or to the appearance or the development of cataracts.

It was notably noticed that the presence of corticosteroids in the anterior segment of the eye was in particular related to the appearance of these side effects, and was thus undesirable.

The need to administrate the corticosteroids the most locally possible, therefore selectively in the disease site, in effective quantities, was then clear.

The effectiveness of the treatment is in particular related to the presence of the active compound and hence to the half life of the drug. A known corticosteroid, the dexamethasone has a half life of 3.5 hours when injected intraocularly (Kwak, Arch Opthalmol, 1992). Thus, the injections must be repeated to maintain a therapeutic effect.

However, repeated injections are difficult to cope with for the patients suffering of long or chronic diseases. Moreover, repeated injections are likely to increase harmful side effects such as retina detachment, endophtalmy, and cataracts.

In view of the additional side effects caused by repeated injections, intraocular implants of steroids have been developed:

RETISERT™ (fluocinolone acetonide intravitreal implant, Bausch & Lomb) 0.59 mg is a sterile implant designed to release fluocinolone acetonide locally to the posterior segment of the eye. RETISERT™ was recently approved by the FDA and is indicated for the treatment of chronic non-infectious uveitis affecting the posterior segment of the eye. However, clinical trials of this implant systematically results in a raise of the intraocular pressure (IOP) and cataracts as main adverse effects. Holekamp et al. found that after long-term follow-up, high-dose intraocular fluocinolone acetonide results in significant complications rate, with 100% of the eyes developing elevated IOP and 30% showing nonischemic central retinal vein occlusion. These complications required the implant removal in almost 60% of the eyes (Am J Opthalmol 2005). Implantation of 0.59 mg or 2.1 mg fluocinolone acetonide in noninfectious posterior uveitis patients results in a 5-fold augmentation of the need of IOP lowering agents (Jaffe, Opthalmology, 2005). In a randomized clinical trial of 0.59 mg fluocinolone acetonide intravitreal implant in patients with diabetic macular edema, the most common adverse included serious cataract progression (43.1%) and a serious intraocular pressure rise (8.6%) (Pearson, ISOPT communication, Berlin, 2006). Based on clinical trials with RETISERT, within 34 weeks post-implantation, approximately 60% of patients will require IOP lowering medications to control intraocular pressure. Within an average postimplantation period of approximately 2 years, approximately 32% of patients are expected to require filtering procedures to control intraocular pressure. Moreover, within an average post-implantation period of approximately 2 years, nearly all phakic eyes are expected to develop cataracts and require cataract surgery (source Bausch & Lomb).

Posurdex is another intraocular device being developed by Allergan containing 700 micrograms of dexamethasone which are released during the first month post implantation. Its efficacy has been evaluated among others in cases of persistent macular edema (Williams, ISOPT communication, 2006) and for anti-inflammatory effects after cataract surgery (Tan, Opthalmology, 2004). However, a safety and efficacy clinical study of 700 micrograms dexamethasone implant for the treatment of macular edema showed significant increases in IOP (to $\geq 25$ mm Hg) in 15% of patients (Williams, ISOPT communication, Berlin, 2006).

The off-label use of triamcinolone acetonide (Kenalog 40™, Bristol Myers Squib) intraocularly results indirectly in the slow-release of the drug, as the insoluble steroid precipitates following injection in the vitreous cavity and is only gradually solubilized. Therefore, it can be considered as well as a sustained release steroidal formulation. However, this formulation which was not originally developed for intraocular use can cause serious complications such as infectious endophthalmitis and sterile endophthalmitis, retinal toxicity and crystalline retinal deposits. Nevertheless, it has been used intravitreally to treat ocular inflammation as well as macular edema due to numerous causes. In addition, retrospective analysis of subtenon triamcinolone acetonide cases also reveals intraocular pressure rise in 21% of the patients (Bui Quoc, J Fr Ophtalmol, 2002).

Other steroid-containing devices being developed in research are triamcinolone acetonide/polycaprolactone implants (Beeley, J Biomed Mater Res A, 2005), triamcinolone/polyvinyl alcohol implants (Ciulla, Br J Opthalmol, 2003), betamethasone polymeric implants (Kato, IOVS, 2004 and Okabe, IOVS, 2003) and others.

This analysis of the intraocular corticosteroid-containing implants shows that the long lasting presence of corticosteroid in the posterior segment of the eye causes undesirable side effects, even though the therapeutic effect is undoubtful.

There is need therefore for an ophthalmic device or composition which will succeed in delivering a therapeutic amount of active steroid in a satisfactory manner for the patient, i.e. ensuring safety and avoiding any toxic effect, especially avoiding undesirable systemic side effect of the intraocularly administered steroid.

One goal of this invention is to provide a composition, delivering a therapeutic amount of active steroid for a sustained period in the eye. Preferably, the composition of the invention delivers a therapeutic amount of steroid in the disease site. More preferably, the composition of the invention delivers the therapeutic amount of steroid needed to treat the very pathology of the patient. According to this embodiment, the composition of the invention is of great interest for personalized methods of treatment. Another goal of this invention is to increase the comfort of the patient by reducing the number of needed injections. As intraocular injections are particularly uncomfortable, this further goal is of importance for the patient.

From this assumption, the inventors searched alternative therapeutic pathways for an efficient administration of steroids, preferably corticosteroids inside the eye: this invention relates to the use of prodrugs of steroids, especially corticosteroids, for the preparation of a medicament or an ophthalmic composition intended for the treatment of an ocular condition or disease of a human being or an animal, said medicament or ophthalmic composition being administered by invasive means, preferably by intraocular injection, more preferably by intravitreal injection, for in-situ sustained release of therapeutic effective agents.

The inventors observed that intraocular, more especially intravitreal, injections of a corticosteroid prodrug, the dexamethasone palmitate, resulted in the in-situ release of dexamethasone.

Without wanting to being linked by a theory, the Inventors suppose that there might be a selective uptake of the steroid prodrug, preferably a lipophilic ester of a steroid, by the ocular inflammatory cells (macrophages). The increased macrophage activity at the inflamed sites may result in a targeted cleavage of the active moiety only in the disease location, with no unspecific release. Therefore, fewer side effects occasioned by the therapeutic agent are expected to be observed. The drug would be release at the very location of the disease, resulting in a decrease of unwanted adverse effects in other ocular structures where the prodrug is not hydrolyzed. The invention also permits maintaining the desired effect in the ocular condition for an extended period of time during which an amount of the prodrug is present at the ocular site such that it allows the release of an effective amount of the active drug for an extended period of time, which is preferably at least one month. Thus, the present invention also relates to a method of personalized treatment of a patient in need of a steroid intraocular treatment: each patient, as of he/she is administered with prodrug of the invention, may intraocularly release the exact amount of needed active steroid according to his stage of development of his/her pathology, thus avoiding side effects due to extra and unneeded amounts of active steroids in the vitreous body.

A further advantage of this invention is that no systemic side effect was observed when intraocularly administering the ester of steroid of the invention. Moreover, the usual side effect linked to the presence of high amounts of steroids in the vitreous body, i.e. intraocular pressure, was not observed when administering high amounts of the prodrug, i.e. ester of steroid, of the invention. Another advantage of this invention is that the prodrug of the invention, when administered, may remain in the vitreous body as such, resulting in the vitreous body being a storage of ready-to-be-released inactive prodrug. A further advantage of the invention is that, due to absence of side effects of the inactive prodrug and due to the sustained released of the steroid from the prodrug, the amount of prodrug to be possibly administered into the eye may be much more important than the amount of active (and toxic) drug. Accordingly, the number of injections may be decreased. According to an embodiment, the frequency of injection is of once a month or less, preferably equal or less than once every 2 months, more preferably equal or less than once every three months, most preferably equal or less than once every four, five or six months.

By "prodrug" in the invention is meant an ester of steroid, preferably a lipophilic long-chain ester of steroid, preferably of corticosteroid, said ester group comprising an alkyl group of more than 10 carbons preferentially of more than 14 carbons, even more preferentially of 16 carbons being preferably directly linked to a function of the steroid. According to an embodiment, the ester of steroid of the invention does not include a phosphate group. According to the invention, the ester group is of formula —COOR or —OC(O)R, wherein R is a long alkyl or alkenyl chain, preferably a C4-C16 alkyl chain, even more preferably C12, C14, C16, C18, C20 saturated or unsaturated chain, more preferably any suitable lipophilic chain.

According to a preferred embodiment of the invention, the prodrug does not have any direct therapeutic and/or physiologic effect, and is therefore called "inactive", whereas the drug released by hydrolysis of the prodrug does have a physiological therapeutic effect. On the contrary, by "active" steroid, in the meaning of this invention, is meant a steroid that has a direct therapeutic and/or physiologic effect. Thus, a difference has to be made between steroids or steroid derivatives that are therapeutically directly effective, and are "active" steroids or steroid derivatives in the meaning of this invention, versus "inactive" esters of steroid, i.e. the prodrugs of the invention.

The invention is directed to the use of a composition comprising at least one prodrug of a steroid, preferably of a corticosteroid, for the preparation of an ophthalmic composition intended for the treatment of an ocular condition or disease of a human being or an animal.

The composition according to the invention comprises at least one prodrug of corticosteroid, which is preferably selected from: alclometasone dipropionate, amcinonide, amcinafel, amcinafide, beclamethasone, betamethasone, betamethasone dipropionate, betamethasone valerate, clobetasone propionate, chloroprednisone, clocortelone, Cortisol, cortisone, cortodoxone, difluorosone diacetate, descinolone, desonide, defluprednate, dihydroxycortisone, desoximetasone, dexamethasone, deflazacort, diflorasone, diflorasone diacetate, dichlorisone, esters of betamethasone, fluazacort, flucetonide, flucloronide, fludrotisone, fluorocortisone, flumethasone, flunisolide, fluocinonide, fluocinolone, fluocinolone acetonide, flucortolone, fluperolone, fluprednisolone, fluoroandrenolone acetonide, fluocinolone acetonide, flurandrenolide, fluorametholone, fluticasone propionate, hydrocortisone, hydrocortisone butyrate, hydrocortisone valerate, hydrocortamate, loteprendol, medrysone, meprednisone, methylprednisone, methylprednisolone, mometasone furoate, paramethasone, paramethasone acetate, prednisone, prednisolone, prednidone, triamcinolone acetonide, triamcinolone hexacatonide, and triamcinolone, salts, derivatives, and a mixture thereof.

More preferably, the corticosteroid is selected from: cortisone, dexamethasone, fluocinolone, hydrocortisone, methylprednisolone, prednisolone, prednisone, and triamcinolone. In this embodiment, the composition of the invention comprises a prodrug of cortisone, dexamethasone, fluocinolone, hydrocortisone, methylprednisolone, prednisolone, prednisone, and triamcinolone.

In the most preferred embodiment of the invention, the composition comprises a prodrug of dexamethasone, more preferably dexamethasone palmitate.

In another preferred embodiment, the composition comprises a long-chain ester of steroid, preferably a C12-C18 ester of steroid, more preferably dexamethasone stearate, dexamethasone laurate, triamcinolone palmitate, triamcinolone stearate, triamcinolone laurate, triamcinolone acetonide palmitate, triamcinolone acetonide stearate, triamcinolone acetonide laurate.

Preferably, the prodrug is comprised in the emulsion in an amount of about 0.01% to about 10% w/w of the emulsion, preferably 0.05% to 5% w/w, more preferably 0.1 to 1% w/w. According to an embodiment, the prodrug is comprised in the amount of about 0.5% to about 3% w/w of the composition, which preferably is an emulsion. In a preferred embodiment, the prodrug is comprised in a amount of about 2% w/w of the composition, which preferably is an emulsion. In another preferred embodiment of the present invention, the prodrug is comprised in an amount of about 1% w/w of the composition, which preferably is an emulsion.

In an embodiment of the invention, the amount of prodrug to be administrated is an amount therapeutically equivalent to 0.01-6 µmol of steroid, preferably Dexamethasone, preferentially equivalent to 0.1 to 2.5 µmol of steroid, preferably Dexamethasone, and most preferentially equivalent to 0.15-1.3 µmol of steroid, preferably Dexamethasone.

In a further embodiment the molar amount of ester of steroid administered is higher than the highest non-toxic molar amount of said steroid injected by the same administration mode.

In a preferred embodiment of the invention, the amount of prodrug to be administrated is an amount therapeutically equivalent to 0.1 to 2.5 mg of Dexamethasone.

In another preferred embodiment, the amount of Dexamethasone Palmitate to be administrated is in the range of 0.1 to 3.2 mg, preferentially 0.2 to 1 mg and most preferentially 0.4 to 0.8 mg.

According to an embodiment, the aqueous solubility of the prodrug of the invention is of less than 120 µg/mL, preferably of less than 50 µg/mL and more preferably of less than 10 µg/mL.

According to the invention, the composition of the invention includes at least one steroid prodrug dissolved in a opthalmologically acceptable oil.

According to an embodiment of the invention, the carrier is selected from (1) an oil; examples of suitable oily carrier are mineral oils such as silicone, paraffin or vegetal oils such as medium chain triglycerides, soybean castor oil, olive oil, corn oil, palm oil or any other oil suitable for intraocular injection, preferably selected from MCT, castor oil and soybean oil, or from (2) an emulsion where the oil phase preferably is selected from mineral oils such as silicone, paraffin or vegetal oils such as medium chain triglycerides, soybean castor oil, olive oil, corn oil, palm oil or any other oil suitable for intraocular injection According to an embodiment of the invention, the weight ratio prodrug/oil is 0.04 to 0.3.

According to a preferred embodiment of the invention, the ratio Dexamethasone Palmitate/Soya bean oil is 0.04 to 0.3.

According to another embodiment of the invention, the composition of the invention includes at least one steroid prodrug dissolved in a physiologically acceptable oil which is emulsified into a oil-in-water emulsion by different techniques such as high shear and high pressure homogenization with suitable emulsifiers; final preparation can be sterilized by filtration or by autoclave.

According to an embodiment of the invention, the composition comprises at least one prodrug as above-defined, in combination with any ophtalmologically acceptable excipient or carrier. The carrier may be selected from an ophtalmologically acceptable oil, phospholipid vesicles or oil-in-water emulsion or water-in-oil emulsion or any other suitable carrier about 20, at least about 30 or at least about 40 weight percent of the composition/emulsion, preferably 10% of the emulsion.

Excipient characteristics that are considered include, but are not limited to, the biocompatibility and biodegradability at the site of implantation, compatibility with the prodrug of interest, and processing temperatures.

When the excipient or the carrier is an emulsion, according to an embodiment of the invention, the oil phase represents at least about 1, at least about 5, at least about 10, at least about 20, at least about 30 or at least about 40 weight percent of the composition. In a preferred embodiment, the oil represents 10 weight percent of the composition. In this embodiment, the composition includes at least one surfactant, preferably in an amount of 0.1-10% w/w of the composition. According to an embodiment, the surfactant is selected from phospholipids, poloxamers, tyloxapol, polysorbate, and polyoxyethylene fatty acid esters. In this embodiment, the composition preferably includes at least one isotonicity agent, preferably in an amount of 0.1-10% w/w of the composition. According to an embodiment, the istonicity agent is glycerol.

Preferably, the composition of the invention is as follows:

| Role | Amount (w/w) |
| --- | --- |
| Prodrug | 0.01-10% |
| Oil | 1-40% |
| Surfactant | 0.1-10% |
| Tonicity agent | 0.1-10% |
| Dispersing medium | Up to 100% |

According to an embodiment, the composition of the invention is as follows:

| Role | Amount (w/w) |
| --- | --- |
| Prodrug | 0.1-5% |
| Oil | 8-12% |
| Surfactant | 0.5-2% |
| Tonicity agent | 1-3% |
| Dispersing medium | Up to 100% |

In the meaning of this invention the term "about" means approximately or nearly and in the context of a numerical value or range set forth herein means .+/−0.10% of the numerical value or range recited or claimed.

According to an embodiment of the invention, the composition of the invention is administered through one intraocular injection, more preferably through one intravitreal injection.

According to another embodiment of the invention, the composition of the invention is administered through the placement of an intraocular implant containing or combined with the composition of the invention.

According to another embodiment of the invention, the composition further comprises an active agent selected from cyclosporine, anti-VEGF, and/or an antibiotic.

According to another embodiment of the invention, wherein the composition comprises dexamethasone palmitate and at least one active agent selected from the group consisting of cyclosporine, anti-VEGF, and an antibiotic.

The invention also relates to a method of treatment of a human or animal ophthalmic condition or disease comprising the intraocular administration of the composition of the invention.

According to an embodiment, the method of the invention includes the administration of a steroid prodrug into an ocular site of a patient suffering from an ocular condition or disease. The prodrug can be administered alone or in an ophtalmologically carrier suitable for intraocular administration. The carrier may be a surfactant solution, oil, phospholipid vesicles or oil-in-water emulsion, or any other suitable carrier.

The administrated prodrug will gradually release through its hydrolysis by endogenous enzymes in situ, to generate therapeutic levels of the active drug in the disease site. This results in the improvement of ocular conditions by the action of the active drug in the very site of inflammation due to the ocular condition or disease.

According to an embodiment of the invention, the release of the steroid is in amount dependant from the condition of the patient: the more serious the condition is, the more the release of the steroid occurs. This means that a more serious condition leads to the release of a bigger amount of steroid: thus, the treatment is adapted to the severity of the condition of the patient. This invention thus relates to a method for administering the exact amount of steroid necessary to treat his specific condition.

According to an embodiment of the invention, the frequency of administration of the composition of the invention trough injection is once a month, preferably once every two months, more preferably once every six months. It is an advantage of this invention to provide a less frequent need for repeated administration.

According to an embodiment of the invention, the amount of the composition of the invention administered is such that, after one month, the molar ratio drug/prodrug in the target tissue, preferably in choroid or in retina, is equal or less than 1, preferentially of 0.5, more preferentially of 0.1.

According to one embodiment of the invention, the composition of the invention is in the form of a solution, an emulsion, a suspension. Examples of the composition of the invention are the following:

Composition A

| Role | Component | Amount (w/w) |
| --- | --- | --- |
| Active agent | Dexamethasone palmitate | 0.8% |
| Oil | MCT | 10% |
| Surfactant | Lipoid E-80 | 1.5% |

| Role | Component | Amount (w/w) |
| --- | --- | --- |
| Tonicity agent | Glycerol | 2.2% |
| Dispersing medium | Water | Up to 100% |

Composition B

| Role | Component | Amount (w/w) |
| --- | --- | --- |
| Active agent | Dexamethasone palmitate | 0.4% |
| Oil | Soybean oil | 10% |
| Surfactant | Lipoid E-80 | 1.5% |
| Tonicity agent | Glycerol | 2.2% |
| Dispersing medium | Water | Up to 100% |

Composition C

| Role | Component | Amount (w/w) |
| --- | --- | --- |
| Active agent | Triamcinolone palmitate | 5% |
| Oil | MCT | 10% |
| Surfactant | Lipoid E-80 | 1.5% |
| Tonicity agent | Glycerol | 2.2% |
| Dispersing medium | Water | Up to 100% |
| Active agent | Dexamethasone palmitate | 0.5% |
| Solubilizing agent | PEG200 | Up to 100% |

The improvement of the ocular condition obtained by a method within the scope of the present invention can be determined by observing: an improved visual acuity, an improved visual contrast sensitivity, a decreased retinal or choroidal blood vessel leakage, a decreased retinal or macular thickness, or a reduced number of cells in the aqueous or vitreous humor or by determining a reduced flare.

According to an embodiment of the invention, the administration of the composition of the invention is invasive. More preferably, the composition of the invention is administered through an implant or through intraocular, preferably intravitreal injection.

The compositions of the invention are useful for the treatment of conditions or diseases affecting the interior of the eye, preferably of the back of the eye. These compositions are especially useful for the treatment of the following conditions or diseases: uveitis, macular edema, macular degeneration, retinal detachment, ocular tumors, bacterial, fungal but viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion.

In a preferred embodiment, the composition of the invention is within an implantable device and then used for the treatment of uveitis, macular oedema, vascular occlusive conditions, proliferative vitreoretinopathy (PVR), and various other retinopathies. In view of the advantages of the present invention for the patient, in term of lack of toxicity, comfort of limited number of injection, storage of ready-to-be released drug, it should be considered in the future of very limited interest to directly administering toxic steroid.

The invention is further illustrated by the following example, which should not be considered in any way as a limitation the scope of the protection.

EXAMPLES

1. Analytical Methods for Simultaneous Determination of Dexamethasone and Dexamethasone Palmitate in Ocular Tissues A liquid chromatographic-mass spectrometric method for the simultaneous determination of dexamethasone and dexamethasone palmitate in ocular tissues was developed. Analytes and internal standard (roxithromycine) were extracted from the tissues using acetonitrile and separated by reverse phase liquid chromatography with a C8 column and a gradient mobile phase. The compounds were detected by mass spectrometric detection (atmospheric pressure ionization) with selected ion monitoring (SIM) (393.0 for dexamethasone and 631.5 for dexamethasone palmitate). The method was selective for both compounds and the limits of quantification were 32.7 ng/g of retina and 71.6 ng/g choroid. The unweighed linear model was applied.

2. Intraocular Pharmacokinetics of Dexamethasone Palmitate and Dexamethasone Following Intravitreal Administration Methods:

One single unilateral intravitreal injection of a 0.8% (8 mg/ml) dexamethasone palmitate emulsion to rabbits (100 μL). Sacrifice at days 1, 7, 14, 21, 28 or 60 days (n=4/timepoint). Dexamethasone (D) and dexamethasone palmitate (DP) in tissues were determined. All concentrations are expressed in nmol/g tissue.

Results:

|  |  | Day 1 | | Day 7 | | Day 14 | | Day 28 | | Day 60 | |
| --- | --- | --- | --- | --- | --- | --- | --- | --- | --- | --- | --- |
|  |  | Mean | sd | Mean | sd | Mean | sd | Mean | sd | Mean | sd |
| Retina | DP (nmol/g) | 106 | 74 | 93 | 38 | 136 | 19 | 146 | 109 | 55 | 37 |
|  | D (nmol/g) | 7 | 2 | 11 | 4 | 6 | 4 | 4 | 1 | 2 | 2 |
|  | D/DP | 0.660 | | 0.118 | | 0.044 | | 0.027 | | 0.036 | |
| Choroid | DP (nmol/g) | 191 | 69 | 103 | 77 | 22 | 11 | 143 | 61 | 52 | 22 |
|  | D (nmol/g) | 12 | 6 | 12 | 7 | 9 | 4 | 4 | 1 | 3 | 2 |
|  | D/DP | 0.063 | | 0.117 | | 0.409 | | 0.028 | | 0.057 | |
| Aqueous humor | DP (nmol/g) | ND | ND | ND | ND | ND | ND | ND | ND | 0 | 0 |
|  | D (nmol/g) | ND | ND | ND | ND | ND | ND | ND | ND | 0 | 1 |

ND: Not determined.

Following IVT injection of a dose of 800 μg of prodrug, dexamethasone of more than 800 ng/g (higher than therapeutic levels) were maintained for at least 2 months in the target tissues. Moreover, considerable amounts of the prodrug dexapalmitate remained in both retina and choroid, indicating an even more long-lasting release.

At the same time, the amount of steroid in the aqueous humor was undetectable, suggesting fewer (if any) side effects in adjacent sites. This last fact was corroborated by IOP measurements, which were normal 2 months following the injection.

The invention claimed is:

1. A method of treating an ocular condition or disease of a human being or an animal, comprising
   intravitreally administering to a posterior segment of an eye by an invasive means of intraocular injection a medicament or an ophthalmic composition, wherein,
   said medicament or said ophthalmic composition comprises from 0.8% to about 5% w/w inactive dexamethasone palmitate,
   said inactive dexamethasone palmitate is hydrolyzed by endogenous enzymes in the posterior segment of the eye to release active dexamethasone for treating said condition or said disease, and
   said condition or said disease is of the back of the interior of the eye selected from the group consisting of: macular edema, macular degeneration, retinal detachment, ocular tumors, bacterial, fungal and viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion.

2. The method according to claim 1, wherein said medicament or said ophthalmic composition comprises about 0.8% to about 3% w/w of said dexamethasone palmitate.

3. The method according to claim 1, wherein said dexamethasone palmitate is in combination with any ophthalmically acceptable excipient or carrier, or within an implant.

4. The method according to claim 3, wherein said dexamethasone palmitate is in combination with a carrier selected from the group consisting of an ophthalmic acceptable oil, phospholipid vesicles, an oil-in-water emulsion and a water-in-oil emulsion.

5. The method to claim 4, wherein the carrier is one of (i)an oil selected from the group consisting of MCT, castor oil and soybean oil, and (ii)an emulsion where the oil phase is selected from the group consisting of MCT, castor oil and soybean oil.

6. The method according to claim 4, wherein,
   the carrier is an emulsion,
   and oil phase comprises at least about 1 weight percent of one of (i) said medicament or said ophthalmic composition and (ii) said emulsion.

7. The method according to claim 1, wherein said dexamethasone palmitate is administered through one intraocular injection every one, two or six months.

8. The method according to claim 1, wherein the amount of said medicament or said ophthalmic composition administered is such that, after one month, the molar ratio dexamethasone/dexamethasone palmitate in the retina or in the choroid is equal or less than 1.

9. The method according to claim 1, wherein said medicament or said ophthalmic composition further comprises an active agent selected from the group consisting of cyclosporine, anti-VEGF, and an antibiotic.

* * * * *